US00PP27224P3

(12) United States Plant Patent
Nuccio et al.

(10) Patent No.: US PP27,224 P3
(45) Date of Patent: Oct. 4, 2016

(54) ***CAMELLIA* PLANT NAMED 'JULIUS NUCCIO'**

(50) Latin Name: *Camellia japonica*
Varietal Denomination: Julius Nuccio

(71) Applicants: Julius J. Nuccio, Los Angeles, CA (US); Thomas Jay Nuccio, Altadena, CA (US); James Edward Nuccio, Altadena, CA (US)

(72) Inventors: Julius J. Nuccio, Los Angeles, CA (US); Thomas Jay Nuccio, Altadena, CA (US); James Edward Nuccio, Altadena, CA (US)

( * ) Notice: Subject to any disclaimer, the term of this patent is extended or adjusted under 35 U.S.C. 154(b) by 0 days.

(21) Appl. No.: 14/544,825

(22) Filed: Feb. 24, 2015

(65) Prior Publication Data

US 2015/0257319 P1 Sep. 10, 2015

Related U.S. Application Data

(60) Provisional application No. 61/966,513, filed on Feb. 25, 2014.

(51) Int. Cl.
*A01H 5/02* (2006.01)

(52) U.S. Cl.
USPC ..... Plt./245

(58) Field of Classification Search
USPC ..... Plt./245
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Camellia* plant named 'Julius Nuccio', characterized by its sturdy upright plant habit; freely branching habit, dense and bushy appearance; leathery emerald green-colored leaves; freely flowering habit; large semi-double flowers with bright crimson-colored petals; flowers face upright to outwardly on strong peduncles; and good garden performance.

1 Drawing Sheet

Botanical designation: *Camellia japonica.*
Cultivar denomination: 'JULIUS NUCCIO'.

BACKGROUND OF THE INVENTION

The present Invention relates to a new and distinct cultivar of *Camellia* plant, botanically known as *Camellia japonica,* and hereinafter referred to by the name 'Julius Nuccio'.

The new *Camellia* plant originated from an open-pollination in Altadena, Calif. of an unnamed selection of *Camellia japonica,* not patented, as the female, or seed, parent with an unknown selection of *Camellia japonica* as the male, or pollen, parent. The new *Camellia* plant was discovered and selected by the Inventors as a single plant from within the progeny of the stated open-pollination in a controlled environment in Altadena, Calif. in 2005.

Asexual reproduction of the new *Camellia* plant by terminal cuttings taken in a controlled greenhouse environment in Altadena, Calif. since 2005, has shown that the unique features of this new *Camellia* plant are stable and reproduced true to type in successive generations.

SUMMARY OF THE INVENTION

Plants of the new *Camellia* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'Julius Nuccio'. These characteristics in combination distinguish 'Julius Nuccio' as a new and distinct cultivar of *Camellia:*

1. Sturdy upright plant habit.
2. Freely branching habit, dense and bushy appearance.
3. Leathery emerald green-colored leaves.
4. Freely flowering habit.
5. Large semi-double flowers with bright crimson-colored petals.
6. Flowers face upright to outwardly on strong peduncles.
7. Good garden performance.

Plants of the new *Camellia* differ from plants of the female parent primarily in flower form and flower size as flowers of plants of the new *Camellia* are larger and have more petals than flowers of the female parent selection.

Plants of the new *Camellia* can be compared to the plants of *Camellia japonica* 'Tom Knudsen', not patented. In side-by-side comparisons conducted in Altadena, Calif., plants of the new *Camellia* differed from plants of the 'Tom Knudsen' in the following characteristics:

1. Plants of the new *Camellia* were denser and bushier than plants of 'Tom Knudsen'.
2. Plants of the new *Camellia* had larger flowers than plants of 'Tom Knudsen'.
3. Flowers of plants of the new *Camellia* faced outwardly whereas flowers plants of 'Tom Knudsen' were drooping.

Plants of the new *Camellia* can also be compared to the plants of *Camellia japonica* 'Colonel Firey', not patented. In side-by-side comparisons conducted in Altadena, Calif., plants of the new *Camellia* differed from plants of the 'Colonel Firey' in the following characteristics:

1. Plants of the new *Camellia* were denser and bushier than plants of 'Colonel Firey'.

2. Plants of the new *Camellia* flowered earlier than plants of 'Colonel Firey'.
3. With development, flowers of plants of the new *Camellia* maintained form and color whereas flowers of plants of 'Colonel Firey' reflexed and faded.

BRIEF DESCRIPTION OF THE PHOTOGRAPHS

The accompanying colored photographs illustrate the overall appearance of the new *Camellia* plant showing the colors as true as it is reasonably possible to obtain in colored reproductions of this type. Colors in the photographs may differ slightly from the color values cited in the detailed botanical description, which accurately describe the colors of the new *Camellia* plant.

The photograph at the top of the sheet comprises a side perspective view of a typical flowering plant of 'Julius Nuccio' grown in a container.

The photograph at the bottom of the sheet is a close-up view of a typical flowering plant of 'Julius Nuccio'.

DETAILED BOTANICAL DESCRIPTION

The aforementioned photographs and following observations and measurements describe plants grown in Altadena, Calif. in five-gallon containers in a polypropylene-covered shadehouse during the winter under cultural practices typical of commercial *Camellia* production. During the production of the plants, day temperatures averaged 21° C. and night temperatures averaged 10° C. Plants were four years old when the photographs and description were taken. In the following description, color references are made to The Royal Horticultural Society Colour Chart, 2007, except where general terms of ordinary dictionary significance are used.

Botanical classification: *Camellia japonica* 'Julius Nuccio'.

Parentage:

*Female, or seed, parent.*—Unnamed selection of *Camellia japonica,* not patented.

*Male, or pollen, parent.*—Unknown selection of *Camellia japonica,* not patented.

Propagation:

*Type.*—By terminal cuttings.

*Time to produce a rooted young plant, summer.*—About three months at air temperatures ranging from 21° C. to 32° C.

*Root description.*—Medium in thickness; off-white in color.

*Rooting habit.*—Moderate branching; moderately dense.

Plant description:

*Plant form and growth habit.*—Perennial evergreen shrub; sturdy upright plant habit; vigorous growth habit.

*Branching habit.*—Freely branching habit; about 14 primary lateral branches develop per plant; dense and bushy appearance.

*Plant height.*—About 88 cm.

*Plant diameter, area of spread.*—About 46 cm.

*Lateral branch description.*—Length: About 69 cm. Diameter: About 8 mm. Internode length: About 2.7 cm to 4.5 cm. Strength: Strong. Aspect: Upright to outwardly. Texture: Smooth, glabrous; woody with development. Color, young stems: Close to N199C. Color, older stems: Close to 199A.

*Leaf description.*—Arrangement: Alternate, single. Length: About 12.5 cm. Width: About 5.3 cm. Shape: Elliptical. Apex: Acute. Base: Attenuate. Margin: Serrate. Venation pattern: Pinnate, arcuate. Texture, upper and lower surfaces: Smooth, glabrous; leathery. Luster, upper surface: Glossy. Luster, lower surface: Matte. Color: Developing leaves, upper surface: Close to N137A. Developing leaves, lower surface: Close to 137B. Fully expanded leaves, upper surface: Close to N137A; venation, close to 146B. Fully expanded leaves, lower surface: Close to 146A; venation, close to 146C.

*Petioles.*—Length: About 8 mm. Diameter: About 3 mm. Texture, upper and lower surfaces: Smooth, glabrous. Color, upper surface: Close to 145A. Color, lower surface: Close to 146C.

Flower description:

*Flower arrangement and appearance.*—Semi-double rotate flowers, flowers terminal and axillary; freely flowering habit with usually about 14 to 15 flowers and flower buds developing per lateral branch; flowers face upright to outwardly.

*Natural flowering season.*—Plants of the new *Camellia* flower continuously during February and March in California.

*Postproduction longevity.*—Plants maintain good flower substance for about seven to ten days on the plant; flowers not persistent.

*Fragrance.*—None detected.

*Flower diameter.*—Large, about 12.5 cm.

*Flower depth.*—About 5.8 cm.

*Flower buds.*—Length: About 4.4 cm. Diameter: About 2.5 cm. Shape: Ovoid. Color: Close to 185A.

*Petals.*—Arrangement: Semi-double flower form; about 16 petals arranged in about four whorls. Length: About 6.5 cm. Width: About 4.8 cm. Shape: Obovate. Apex: Rounded and slightly sinuate. Base: Attenuate. Margin: Entire. Texture, upper and lower surfaces: Smooth, glabrous; satiny. Color: When opening, upper surface: Close to 185A. When opening, lower surface: Close to 183A to 183B. Fully opened, upper surface: Close to 53A; color does not fade with development. Fully opened, lower surface: Close to 185A; color does not fade with development.

*Sepals.*—Arrangement: About nine fused in 2.5 whorls; shallow cup-shaped calyx. Length: About 2.2 cm. Width: About 2 cm. Shape: Elliptical. Apex: Broadly acute. Base: Truncate. Margin: Entire. Texture, upper surface: Smooth, glabrous. Texture, lower surface: Pubescent. Color, upper surface: Close to 145C to 145D. Color, lower surface: Close to 145B to 145D.

*Peduncles.*—Length: About 6 mm. Diameter: About 4 mm. Aspect: About 20° to 45° from stem axis. Strength: Strong. Texture: Smooth, glabrous. Color: Close to 146B.

*Reproductive organs.*—Androecium: Quantity per flower: About 98. Filament length: About 3.8 cm. Filament color: Close to 48A. Anther shape: Lanceolate. Anther length: About 3 mm. Anther color: Close to 161A. Pollen amount: Moderate. Pollen color: Close to 15A. Gynoecium: Quantity of pistils per flower: One. Pistil length: About 3.5 cm. Style length: About 2.6 cm. Style color: Close to 36D.

Stigma shape: Three-parted. Stigma color: Close to 145B. Ovary color: Close to 150D.

*Fruits and seeds.*—Fruit and seed production have not been observed on plants of the new *Camellia.*

Garden performance: Plants of the new *Camellia* have been observed have good garden performance and to be tolerant to rain and wind and to tolerate temperatures from about −9° C. to about 46° C.

Disease & pest resistant: Plants of the new *Camellia* have not been observed to be resistant to pathogens and pests common to *Camellia* plants.

It is claimed:

1. A new and distinct cultivar of *Camellia* plant named 'Julius Nuccio' as illustrated and described.

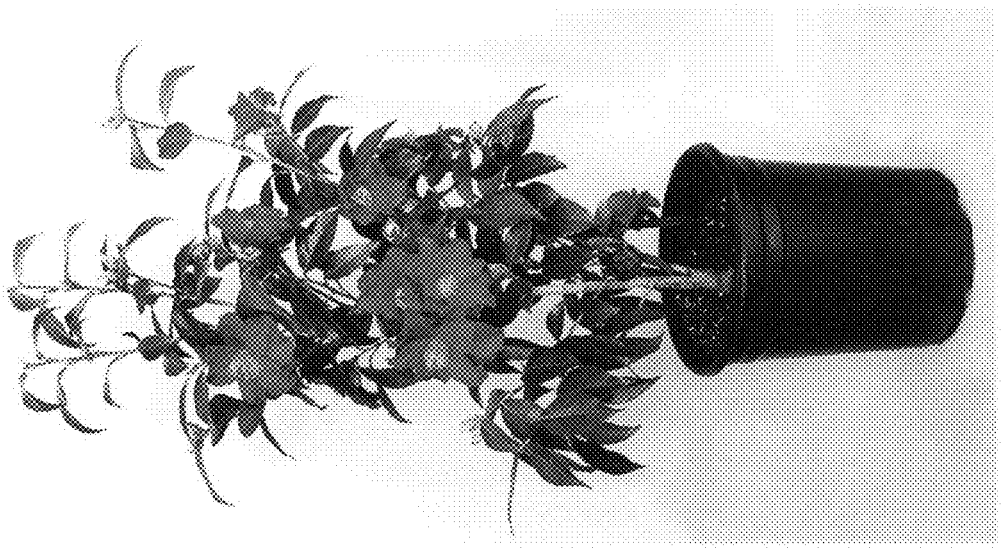
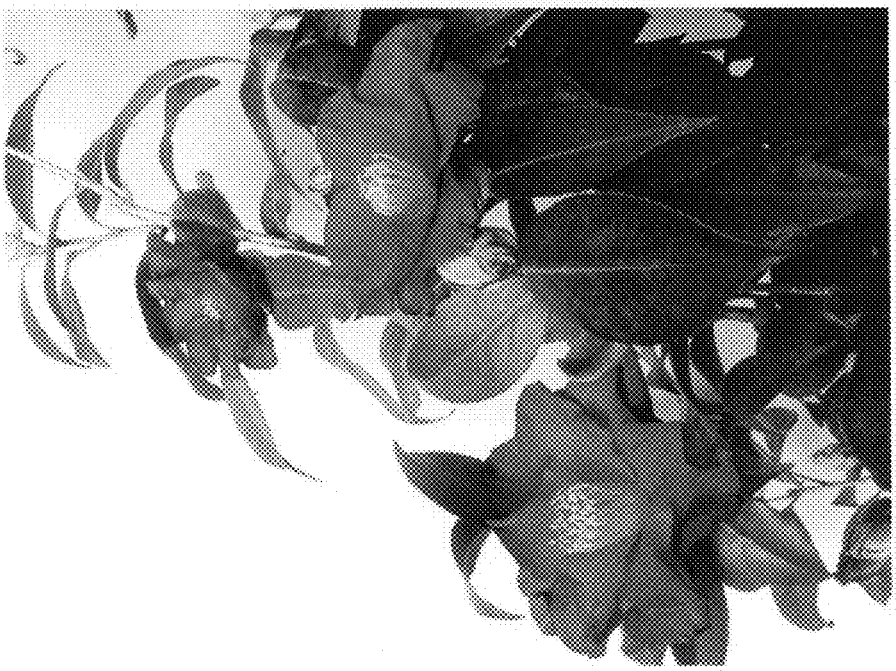

* * * * *